United States Patent
Blomqvist

(10) Patent No.: US 8,700,139 B2
(45) Date of Patent: Apr. 15, 2014

(54) LATE POTENTIAL DETECTION

(75) Inventor: Andreas Blomqvist, Spånga (SE)

(73) Assignee: St. Jude Medical AB, Jarfalla (SE)

( * ) Notice: Subject to any disclaimer, the term of this patent is extended or adjusted under 35 U.S.C. 154(b) by 73 days.

(21) Appl. No.: 13/380,933

(22) PCT Filed: Jun. 26, 2009

(86) PCT No.: PCT/SE2009/000330
§ 371 (c)(1),
(2), (4) Date: Dec. 27, 2011

(87) PCT Pub. No.: WO2010/151181
PCT Pub. Date: Dec. 29, 2010

(65) Prior Publication Data
US 2012/0101397 A1    Apr. 26, 2012

(51) Int. Cl.
*A61B 5/04* (2006.01)

(52) U.S. Cl.
USPC ............. 600/515; 600/510; 607/9; 607/15

(58) Field of Classification Search
USPC ................... 600/510, 515; 607/9, 14
See application file for complete search history.

(56) References Cited

U.S. PATENT DOCUMENTS

| | | | |
|---|---|---|---|
| 5,203,326 A * | 4/1993 | Collins | 607/4 |
| 5,211,179 A | 5/1993 | Haberl et al. | |
| 5,251,621 A | 10/1993 | Collins | |
| 5,609,158 A * | 3/1997 | Chan | 600/518 |
| 5,954,661 A | 9/1999 | Greenspon et al. | |
| 5,983,127 A * | 11/1999 | dePinto | 600/509 |
| 6,058,328 A | 5/2000 | Levine et al. | |
| 7,050,846 B2 | 5/2006 | Sweeney et al. | |
| 7,113,820 B2 * | 9/2006 | Schlegel et al. | 600/523 |
| 7,123,954 B2 | 10/2006 | Narayan et al. | |
| 7,471,980 B2 * | 12/2008 | Koshiol et al. | 607/9 |
| 2002/0177879 A1 * | 11/2002 | Ding et al. | 607/9 |
| 2005/0113705 A1 | 5/2005 | Fischell et al. | |
| 2005/0137633 A1 | 6/2005 | Salo et al. | |
| 2005/0234355 A1 | 10/2005 | Rowlandson | |
| 2007/0118178 A1 | 5/2007 | Fukui | |
| 2009/0227884 A1 | 9/2009 | Saumarez | |

OTHER PUBLICATIONS

"Effects of Different Atrial Pacing Modes Evaluated by Intracardiac Signal-averaged ECG," Kutarski et al., Cardiology Journal, vol. 15 No. 2 (2008) pp. 129-142.

"Endocardial Electrograms From the Right Ventricular Outflow Tracts After Induced Ventricular Fibrillation in Patients With Brugada Syndrome," Ohkubo et al., Circulation Journal, vol. 71, No. (2007) pp. 1258-1262.

"Hypertensive Heart Disease and Endocardially Recorded Late Potentials," Bethge et al. Journal of Cardiovascular Pharmacology, vol. 10, No. S6, pp. S129-S134.

* cited by examiner

Primary Examiner — Michael Kahelin
Assistant Examiner — Mallika D Fairchild

(57) ABSTRACT

A late potential detecting system has an implantable medical device connected to at least one cardiac lead having implantable electrodes positioned at different sites of a ventricle myocardium. A sampling unit of the implantable medical device records electrogram samples for the different implantable electrodes to get different sample sets. The electrogram samples of the sample sets are time synchronized and magnitude potential representations of the potential data of the electrogram samples are determined. The magnitude potential representations of the time synchronized electrogram samples are then co-processed and used for determining a parameter that is indicative of any late potentials of the monitored ventricle.

22 Claims, 8 Drawing Sheets

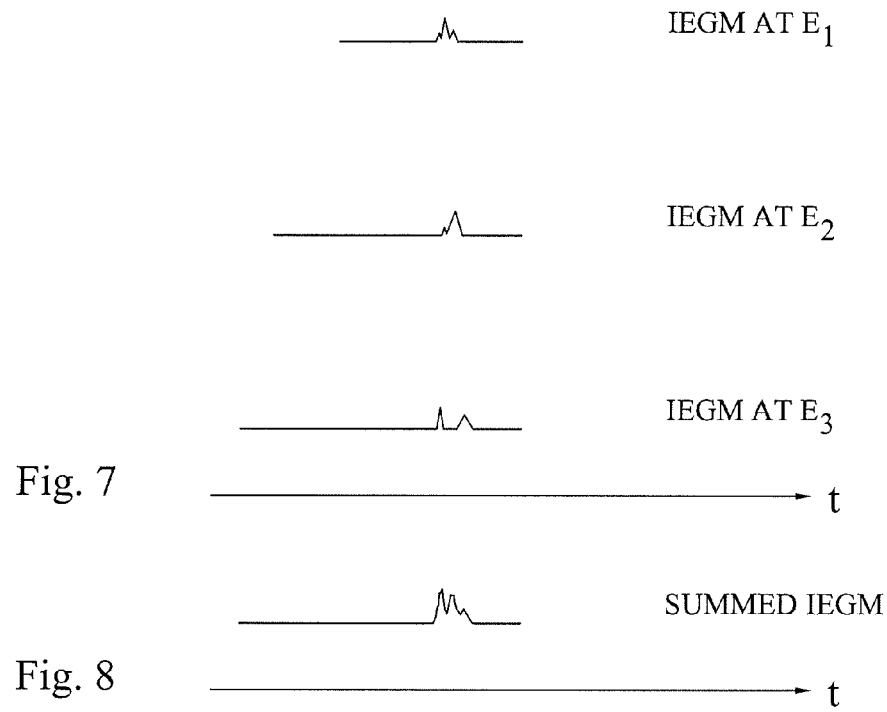
Fig. 7
Fig. 8
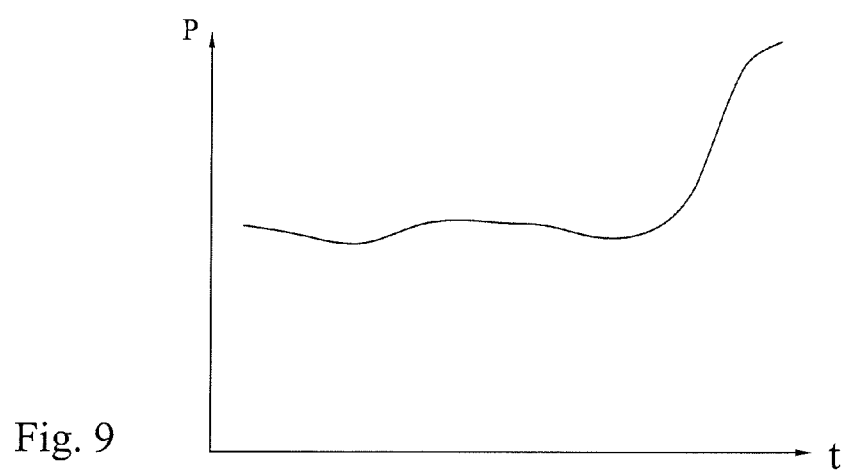
Fig. 9

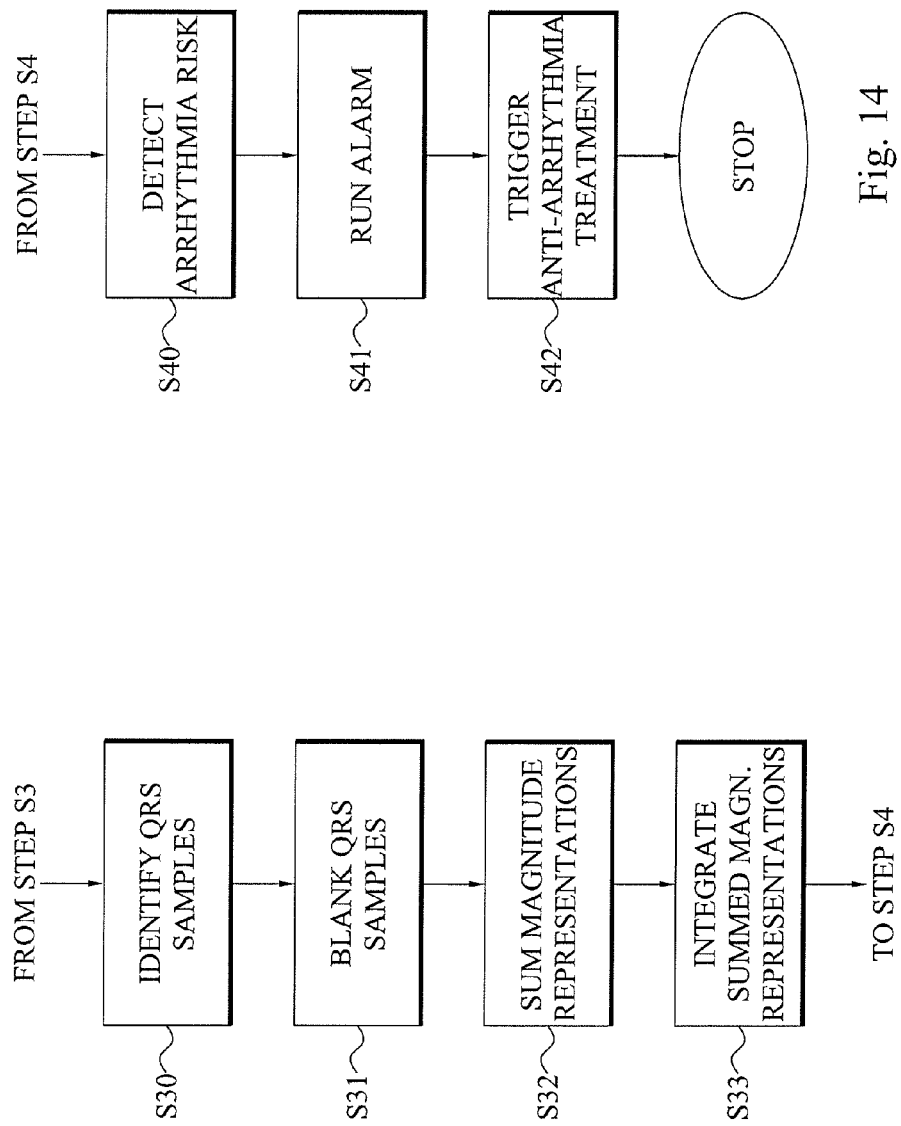

LATE POTENTIAL DETECTION

BACKGROUND OF THE INVENTION

1. Field of the Invention

The present invention generally relates to late potential detection, and in particular to a system comprising an implantable medical device for detecting late potentials of a cardiac ventricle.

2. Description of the Prior Art

Cardiac arrhythmia, sometimes denoted dysrhythmia, encompasses a large heterogeneous group of medical conditions in which there is abnormal electrical activity in the heart of a patient. For instance, the heart may beat too fast or too slow, and may possibly beat regularly or irregularly. Arrhythmias may be benign or potentially life-threatening. Ventricular tachycardia (VT) is an example of the latter and involves fast heart rhythms that originate in one of the ventricles of the heart. This condition is a potentially life-threatening arrhythmia because it may lead to ventricular fibrillation (VF) and sudden death. Ventricular fibrillation involves a multitude of micro-reentry circuits and quivering with chaotic electrical impulses throughout the ventricle(s). Ventricular fibrillation is always a medical emergency and can lead to death within minutes if left untreated. The chaotic electrical impulses in the myocardium of the ventricle significantly reduce the effective blood pumping and may even cause a total stop of the pumping.

Today, more than 450 000 Americans die suddenly each year from sustained ventricular tachycardia or fibrillation. Overall, event rates in Europe are similar to those in the United States.

There is, thus, a great need for being able to detect ventricular tachycardia and/or fibrillation at an early stage in order to put in compensating therapy to stop the arrhythmic condition of the heart. One technique for predicting arrhythmic conditions, such as ventricular tachycardia and fibrillation, is based on the detection of ventricular late potentials (VLP).

Ventricular late potentials represent delayed conduction through a diseased myocardium and are due to the presence of electrical activity in the myocardium of the ventricle after the end of the QRS complex. These aberrant, asynchronous electrical impulses typically arise from viable isolated cardiac muscle bordering an infracted area and are potential substrates for ventricular tachyarrhythmias.

The traditional approach of finding such ventricular late potentials has been to use surface 12-lead electrocardiography (ECG) and so called signal averaged ECG. A patient to be investigated then has to visit a physician to record surface electrograms for multiple consecutive heart cycles. The recorded electrical activity of the heart during these multiple consecutive heart cycles are then signal averaged in a computerized analysis. The physician must then manually investigate the resulting signal averaged ECG in order to detect abnormalities corresponding to ventricular late potentials. Even with the signal averaged ECG it can be very hard to detect any ventricular late potentials, which put high demands on the investigating physician. Signal averaged ECG procedures are disclosed in the art, for instance in U.S. 2005/0234355 and U.S. Pat. No. 6,058,328.

The prior art solutions require the patient to visit the physician at the clinic in order to investigate whether the patient suffers from any ventricular late potentials, which of course is time and cost consuming for both the patient and the healthcare system. Additionally, there is a significant risk of missing patients suffering a risk of arrhythmias using the prior art solution as it may happen that a patient can suffer from ventricular late potentials that come and go. In such a case, there might be no ventricular late potentials detected during the visit at the clinic though the patient may still suffer from ventricular late potentials that occur at other time periods and therefore run a risk of arrhythmias.

There is therefore a need for an automatic solution allowing identification of late potentials of sufficient accuracy and that is not marred by the drawbacks of signal averaged ECGs.

SUMMARY OF THE INVENTION

The present embodiments solve or mitigate the above presented problems of the prior art solutions.

It is an objective to provide an improved late potential detection.

It is a particular object to provide a late potential detection based on an implantable medical device.

Briefly, the present embodiments relate to a late potential detecting system comprising an implantable medical device (IMD). The IMD is in operation electrically connected to at least $N \geq 2$ implantable electrodes of one or more cardiac leads. These implantable electrodes are provided in or in connection with a patient's heart and are arranged for sensing the electrical activity at different sites of the myocardium of one or both heart ventricles. A sampling unit of the IMD records, for each of N implantable electrodes, a sample set of electrogram samples representing the sensed electrical activity of the myocardium during at least a cardiac cycle.

A sample synchronizer of the late potential detecting system processes the electrogram samples of the N sample sets by time synchronizing the electrogram samples. This means that the electrogram samples become time aligned so that corresponding electrogram characteristics captured by the implantable electrodes at different times as the electrical activity propagates over the myocardium of the ventricle are matched between the sample sets. A sample processor determines magnitude potential representations, such as absolute values, of the electrogram samples. The magnitude potential representations of the time synchronized electrogram samples are co-processed by a parameter processor and used for determining a parameter indicative of late potentials occurring in the monitored ventricle during the cardiac cycle.

The sample synchronizer, sample processor and parameter processor can be implemented in the IMD. Alternatively, any of the units can be arranged in an implantable or non-implantable unit optionally constituting a part of the late potential detecting system together with the IMD.

The determined parameter indicative of late potentials is of highly diagnostic value and can be used for risk assessment regarding arrhythmias, such as ventricular tachycardia and fibrillation. The parameter can be determined at high accuracy and resolution and without the intervention of a physician or without the need for physician visits.

Embodiments also relate to a method of detecting late potentials by determining the parameter indicative of late potentials based on the magnitude potential representations of time synchronized electrogram samples representing the electrical activity of different ventricular myocardial sites.

BRIEF DESCRIPTION OF THE DRAWINGS

The invention, together with further objects and advantages thereof, may best be understood by making reference to the following description taken together with the accompanying drawings, in which:

FIG. 7 illustrates the time synchronized IEGMs of FIG. 6 after blanking of QRS samples.

FIG. 8 illustrates a summed IEGM determined based on the time synchronized IEGMs of FIG. 7.

FIG. 9 is a diagram illustrating the trend of a ventricular late potential parameter over time.

FIG. 13 is a flow diagram illustrating additional steps of the late potential detecting method in FIG. 10.

FIG. 14 is a flow diagram illustrating additional steps of the late potential detecting method in FIG. 10.

DESCRIPTION OF THE PREFERRED EMBODIMENTS

Throughout the drawings, the same reference numbers are used for similar or corresponding elements.

The present invention relates to an at least partly implantable system capable of automatically detecting late potentials for a patient, preferably mammalian patient and most preferably a human patient. The system comprises an implantable medical device arranged for sensing electrical activity of the heart of the patient and optionally capable of delivering electric treatment signals to the heart, for instance in the form of pacing pulses, cardioversion shocks and/or defibrillation shocks. The implantable medical device can therefore advantageously be a pacemaker, a defibrillator or a cardioverter.

The at least partly implantable system achieves significant advantages over the prior art late potential detections. For instance, no visits to a healthcare facility for the purpose of acquiring surface 12-lead electrocardiography (ECG) are required as the recording by the system can be conducted automatically without the need for physician visits. The prior art detection further requires a well-experienced heart specialist to investigate the recorded and processed ECG data in order to detect any late potentials. However, even with the experience of the heart specialist, the resolution of the output of such an ECG analysis is very low and the uncertainty is great. Embodiments as disclosed herein provide automatic late potential detection that magnifies the late potential data, thereby increasing the resolution and accuracy of the late potential detection.

Figure 1:
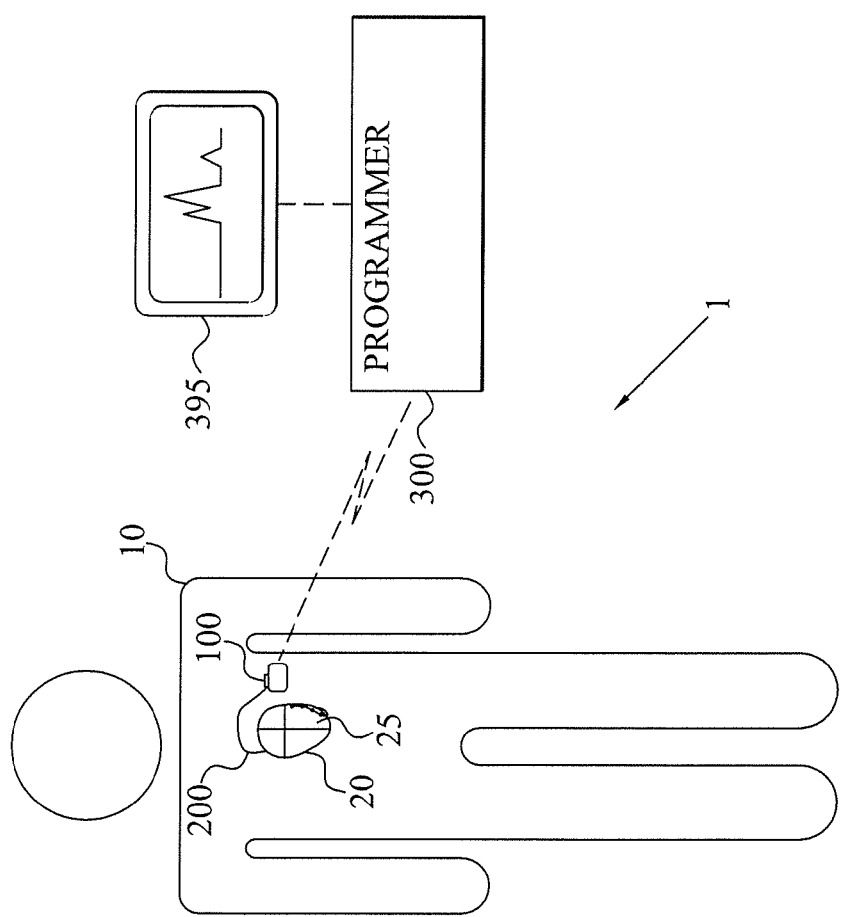
FIG. 1 is an overview of an embodiment of a late potential detecting system having an implantable medical device implanted in a human patient.

FIG. 1 is a schematic overview of a human patient 10 having an implantable medical device (IMD) 100. In the figure, the IMD 100 is illustrated as a device that monitors and/or provides therapy to the heart 20 of the patient 10, such as a pacemaker, cardiac defibrillator or cardioverter. The IMD 100 is, in operation, connected to one or more, one in the figure, cardiac leads 200 inserted into or provided in connection with one or more heart chambers, preferably the left ventricle 25 and/or right ventricle, or being epicardially positioned relative the heart 20.

FIG. 1 illustrates an external programmer or clinician's workstation 300 that can communicate with the IMD 100. As is well known in the art, such a programmer 300 can be employed for transmitting IMD programming commands, using an included transmitter (not illustrated), causing a reprogramming of different operation parameters and modes of the IMD 100. Furthermore, the IMD 100 can upload diagnostic data descriptive of different medical parameters or device operation parameters collected by the IMD 100 to a receiver (not illustrated) of the programmer 300. Such uploaded data may optionally be further processed in the programmer 300 before display to a clinician on a connected display screen 395.

In a particular embodiment, the late potential detecting system can be fully implemented in the IMD 100 or be partly implemented in the IMD 100 and partly implemented in the programmer 300 or indeed in another non-implantable data processing terminal.

Figure 2:
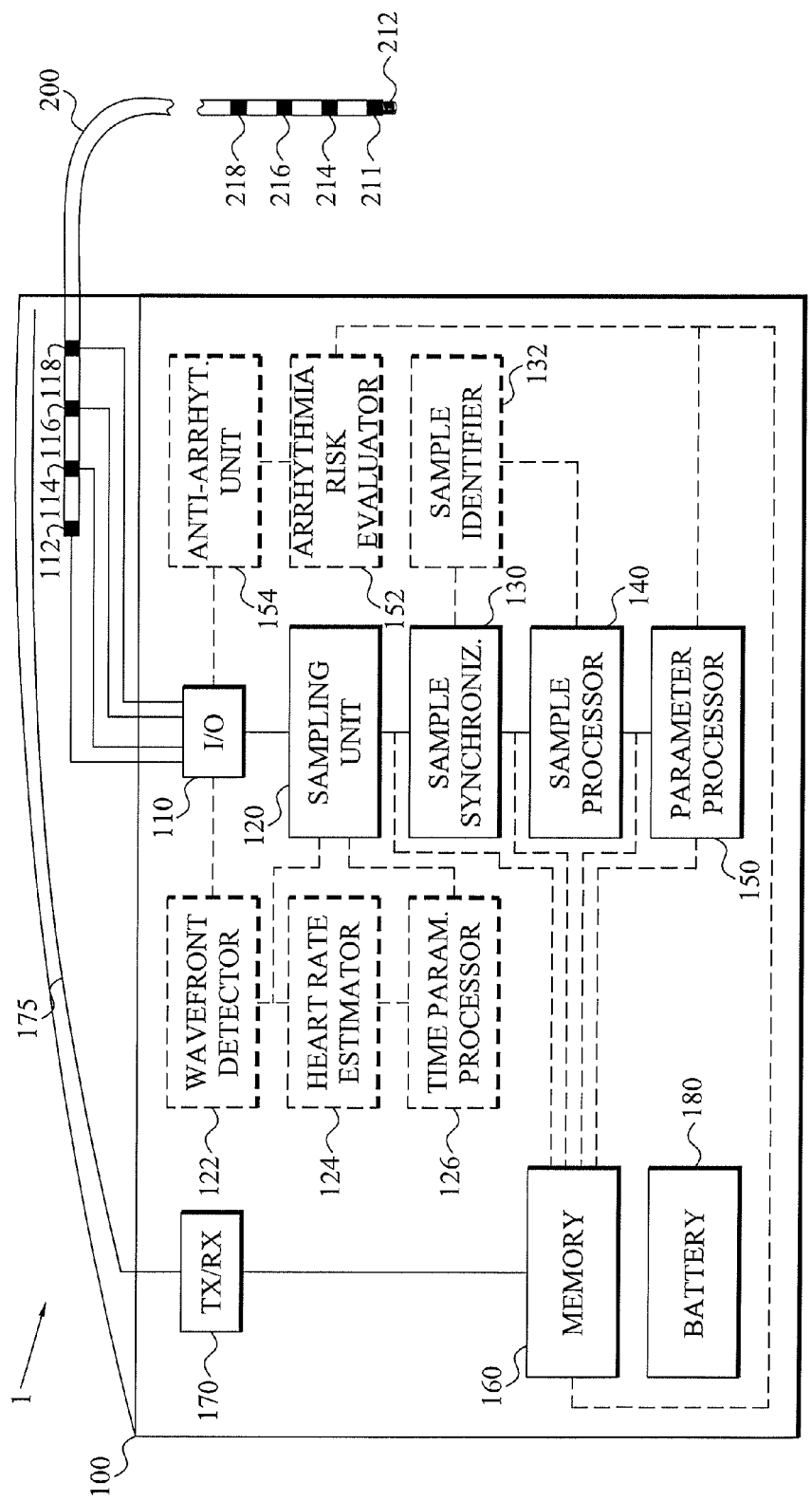
FIG. 2 is a schematic block diagram of a late potential detecting system in the form of an implantable medical device.

FIG. 2 is a schematic illustrating of an embodiment of a late potential detecting system 1. In this embodiment, the detecting system 1 is fully or at least to a major portion implemented and provided in an implantable medical device 100, such as a pacemaker, defibrillator or cardioverter.

The IMD 100 has an electrode input and output (I/O) 110 comprising or being connectable to at least N electrode terminals 112-118. This number N is an integer number equal to or larger than two. In the figure N=4. These electrode terminals 112-118 are arranged in the IMD 100 for electrical connection to respective implantable electrodes 211-218 preferably arranged on one or more cardiac leads 200. The implantable electrodes 211-218 are typically provided at a distal end of the cardiac lead and are, in operation, introduced into or attached close to a ventricle of the heart. In a particular embodiment, the cardiac lead 200 can be a so-called left ventricular lead that is arranged for detecting electrical activity of the myocardium at different parts of the left ventricle using the implantable electrodes 211-218. As is well known in the art, left ventricular leads 200 are typically introduced in the coronary sinus of the heart and are actually seldom introduced in the left ventricle for patient safety reasons. However, the invention can indeed operate with a left ventricular lead actually provided inside the left ventricle. In an alternative embodiment, the cardiac lead 200 is instead a right ventricular lead capable of detecting electrical activity of the myocardium of the right ventricle. Also a combination of a left ventricular lead and a right ventricular lead is indeed possible if detection of late potentials is need for both the left ventricle and the right ventricle.

In order to increase the number of myocardium detection sites, the cardiac lead 200 is preferably a so-called multi-electrode lead 200. This means that the cardiac lead 200 has multiple distinct electrodes that are electrically and spatially isolated from each other to be capable of detecting the electrical activity at multiple sites of the left or right ventricle. Such a multi-electrode lead 200 could be a quadpole lead 200, implying that the cardiac lead 200 comprises four individual electrodes 211-218. These electrodes could be a tip electrode 211 possibly electrically connected to a helical screw 212 that attaches the cardiac lead 200 at the intended site in the heart. In such a case, the helical screw 212 can actually constitute one of the electrodes of the cardiac lead 200. Other solutions for anchoring the cardiac lead 200 to the heart are well-known in the art and can be used instead of helical screws, including passive anchoring techniques. Remaining electrodes 214-218 can be ring electrodes attached at different positions along the length of the cardiac lead 200 as is schematically illustrated in the figure. Alternatively, at least one of the electrodes could be a so called shocking electrode used by cardioverters and defibrillators for applying a high voltage electrical shock to the heart.

There are even multipole leads in the art that comprises more than four electrodes 211-218, such as up to 16 different sensing and/or pacing electrode surfaces provided on a singe cardiac lead.

In order to provide sufficient number of electrodes at different sites of the monitored ventricle(s), the IMD 100 can be connected to two or more left ventricular leads and/or two or more right ventricular leads. If late potential detection is conducted at both ventricles, the detection procedures at the two ventricles are generally run separately either in parallel or one of the ventricles is first analyzed followed by the second ventricle.

The electrode I/O 110 is electrically connected to the electrodes 211-218 of the cardiac leads 200 through conductors running in the lead body from the electrodes 211-218 at the distal end to terminals at the proximal end and through the electrode terminals 112-118 that are electrically and mechanically attached to the terminals at the proximal end. The electrode I/O 110 can also be electrically connected to one or more electrodes that are not provided on the at least one cardiac lead 200. Such an electrode can actually constitute the housing or can of the IMD 100 or at least a portion thereof, which is well known in the art.

The IMD 100 comprises a sampling unit 120 that is connected to the electrode I/O 110. The sampling unit 120 is provided for recording sets of electrogram samples representing the detected or sensed electrical activity of the myocardium of the left ventricle and/or right ventricule during at least one cardiac cycle. The sampling unit 120 preferably records one such sample set for each of the N implantable electrodes 211-218. This means that the samples will contain electrogram data relating to different parts of the myocardium of the monitored ventricle(s) during a cardiac cycle or more than one such cardiac cycle.

The sensed electrical activity from the implantable electrodes 211-218 can be collected through so-called bipolar or unipolar measurements. Also combinations of bipolar and unipolar measurements are possible. The important feature is that the electrogram data of the sampling set should reflect the sensed electrical activity during at least one heart cycle and from different sites of the myocardium of the ventricle. This means that each sample set will contain a number of samples each having a sensed electrical potential at the particular detection site of the sense electrode 211-218 associated with the given sample set.

Figure 5:
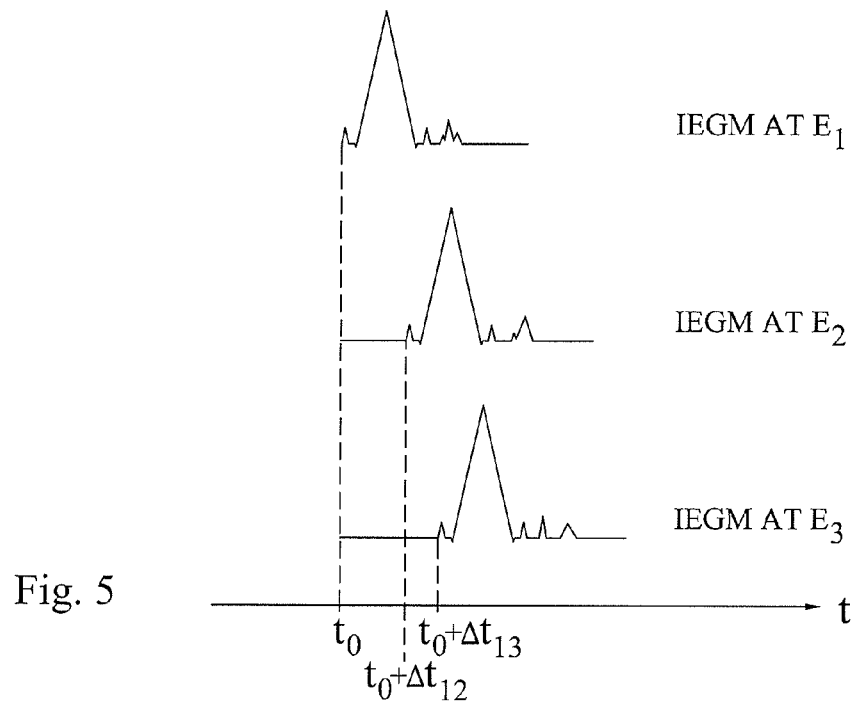
FIG. 5 illustrates sensed IEGM at different implantable electrodes corresponding to a passing wavefront in a ventricle.

A sample synchronizer 130 is provided in the IMD 100 in this embodiment for processing the N sample sets from the sampling unit 120. This sample synchronizer 130 is arranged for time synchronizing the different electrogram sample of the sample sets so that they become time aligned. The reason for this is that during a heart cycle a depolarization or QRS wavefront will travel over the myocardium of the ventricle and arrive at the different sensing electrodes 211-218 at different time instances. FIG. 5 schematically illustrates this concept. The figure illustrates plotted intracardiac electrogram (IEGM) samples collected by three implantable electrodes $E_1$, $E_2$, $E_3$ positioned at three different sites of the ventricles. At time $t_0$ the QRS wavefront is sensed by electrode $E_1$. The same QRS wavefront propagates further and after time $\Delta t_{12}$ (corresponding to $s_{12}$ samples) it has propagated from the site of the electrode $E_1$ to the site of electrode $E_2$. Correspondingly, after time $\Delta t_{13}$ (corresponds to $s_{13}$ samples) the wavefront has propagated further through the myocardium and the ventricle and becomes detected by the third electrode $E_3$.

The sample synchronizer 130 is preferably arranged for synchronizing the N different recordings, i.e. sample sets, so that they are time aligned in the sense that the same wavefront is at the same position in all the channels. The sample synchronizer 130 is typically configured for identifying a respective start electrogram sample of each of the N sample sets. The start sample comprises a predefined electrical characteristic of an electrogram. A typical example could be the start of the QRS complex or some other portion of the QRS complex, such as the sample with the largest magnitude during the QRS complex, i.e. the R wave. Other non-limiting examples of predefined electrical characteristics that can be identified and used as starting samples include the P wave, the Q wave, the R wave and the S wave or any defined portion thereof. Actually any electrical characteristic that can be identified in the provided electrogram samples can be used as long as the same electrical characteristic is used for all the N samples sets.

Figure 6:
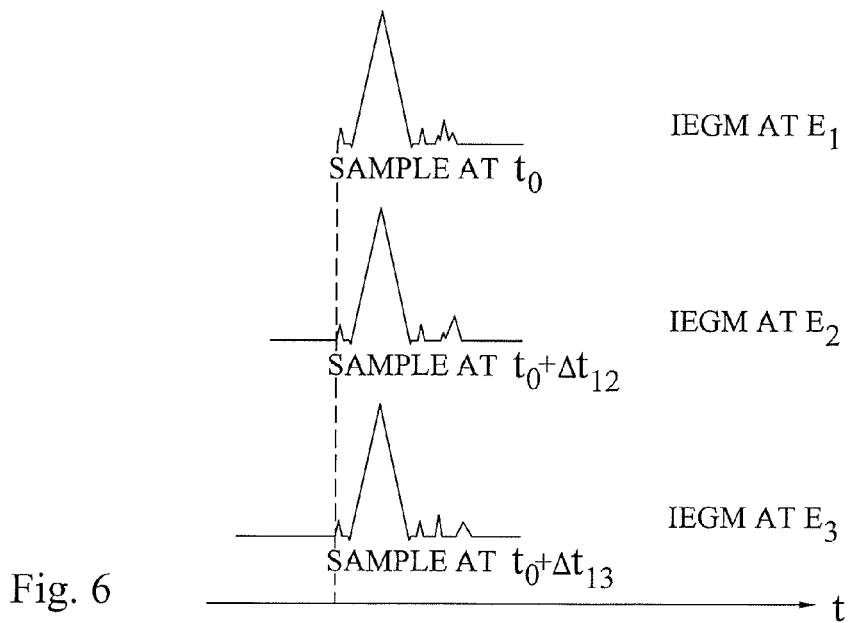
FIG. 6 illustrates the IEGMs of FIG. 5 time synchronized.

The sample synchronizer 130 then synchronizes the electrogram samples of the N sample sets so that the identified start electrogram samples become time aligned. This procedure is visually identified in FIG. 6. The upper diagram illustrates the electrogram data of the first sample set starting with sample $s_0$ corresponding to the start of the QRS complex. The other two sample sets have been shifted so that the start sample $s_0$ of the first sample set is time aligned with sample at $t_0+\Delta t_{12}$ and $t_0+\Delta t_{13}$ for the other two sample sets, respectively.

Note that the sample synchronizer 130 does not necessarily have to time shift the samples of the sample sets in order to achieve the time synchronization. In clear contrast, it is generally enough to mark the samples in each sample set that are identified as the starting sample. This marking can be affected in the form of a list notifying the sample numbers of the different sample sets that correspond to the start samples, such as $s_0$ for electrode $E_1$ ($s_0=f_s \times t_0$, where $f_s$ denotes the sampling frequency of the sampling unit 120), $s_0+s_{12}$ for electrode $E_2$ ($s_{12}=f_s \times \Delta_{12}$), $s_0+s13$ for electrode $E_3$ ($s_{13}=f_s \times \Delta_{13}$), and so on.

Alternatively, all the electrogram samples in the N samples sets that are preceding the respective start samples can be removed so that each sample set then begins with the start sample.

A sample processor 140 of the IMD 100 is configured for determining respective magnitude potential representations of the electrogram samples time synchronized by the sample synchronizer 130. In a typical embodiment, the sample processor 140 simply determines the respective absolute values of the potential data, although other magnitude representations are indeed possible, such as $(P_i)^x$, where $P_i$ denotes the potential data of an electrogram sample and x is an integer equal to or larger than two.

In an alternative embodiment, the sample processor 140 determines the magnitude potential representations for the electrogram samples from the sampling unit 120. The time synchronization conducted by the sample synchronizer 130 is then performed after the determination of the magnitude potential representations.

The magnitude potential representations of the N sample sets are further processed by a parameter processor 150 that is adapted for determining a parameter indicative of late potentials occurring during the monitored cardiac cycle of the ventricle based on the magnitude representations.

The invention has, thus, taken a radically different approach than the prior art when processing electrogram data for the purpose of detecting late potentials and in particular ventricular late potentials (VLPs). In the prior art, recordings over multiple cardiac cycles are conducted using the 12-lead surface echocardiography. These different recordings are then averaged into a template which is used for manual inspection of the occurrence of VLPs. The invention in clear contrast collects electrogram data from multiple sites of a monitored ventricle but during the same cardiac cycle or the same cardiac cycles. This electrogram data is co-processed by the sample synchronizer 130 and sample processor 140 to allow the parameter processor 150 to determine a parameter that is indicative of VLPs based on the processed electrogram data. The inventor has surprisingly discovered that this multi-site monitoring significantly improves the VLP detection and thereby improves the accuracy at which the determined parameter represents VLPs. The reason for this is that combining data from multiple cardiac cycles in the art can actually erase or at least significantly suppress VLPs unless they occur exactly during the same time window of a cardiac cycle. The invention in clear contrast magnifies the VLPs by co-processing data from multiple sites, thereby making the VLPs more easily distinguishable and detectable by the IMD 100.

In a particular embodiment, the IMD 122 optionally comprises a wavefront detector 122 connected to the electrode I/O 110. This wavefront detector 122 is arranged for detecting the presence of an electrical wavefront at an implantable electrode 211-218 based on the electrical activity sensed by the electrodes. The wavefront is typically the depolarization wave propagating over the ventricular myocardium. If the wavefront detector 122 detects such a wavefront at one of the electrodes 211-218 a control signal is generated and forwarded to the sampling unit 120. The sampling unit 120 is responsive to the control signal and either triggers the recording of the electrogram sample or triggers a stop of the recording based on the control signal.

Thus, once the wavefront detector 122 detects the electrical wavefront at one of the implantable electrodes 211-218, it generates the control signal and forwards it to the sampling unit 120. The sampling unit 120 starts recording the electrogram samples at the N implantable electrodes 211-218 to collect the sample sets. Once the wavefront detector 122 detects a subsequent wavefront at an electrode, typically the same electrode at which the previous wavefront was detected, it generates a new control signal. This subsequent wavefront occurs during a subsequent cardiac cycle as compared to the previous cardiac cycle during which the previous wavefront was detected by the wavefront detector 122. The control signal is forwarded to the sampling unit 120, which triggers a stop of the recording of the electrogram samples based on the control signal.

In a preferred embodiment, the sampling unit 120 does not stop the recording of the electrogram samples directly upon reception of the second control signal from the wavefront detector. In clear contrast, the sampling unit 120 preferably starts a preset timer and continues the recording until the expiry of the timer. The reason for this is that if the sampling unit 120 should have stopped the recording directly upon reception of the second control signal, too few recorded electrogram samples could have been obtained for at least one of the implantable electrodes 211-218. The sample synchronizer 130 time synchronzies the electrogram samples from the sample sets as previously described and illustrated in FIG. 6 If the recording would have stopped immediately for all implantable electrodes all the sample sets would contain the same number of electrogram samples. However, after the time alignment, which can be effected by shifting samples for some of the electrodes relative the sample set of the electrode at which the wavefront was first detected, there will be no matching samples in the shifted sample set for the last samples in the non-shifted sample set. Furthermore, it could actually be possible that VLP that occurs after the QRS complex in the electrogram data will not be registered if the recording ends too early. As a consequence, the sample recording is preferably allowed to continue a bit into the following cardiac cycle, i.e. up to the expiry of the preset timer.

Assume that $\Delta t_{1i}$ denotes the difference in time between the detection of a wavefront at a first electrode and detection of the same wavefront having propagated over the ventricle myocardium to an electrode i. In such a case, this time $\Delta t_{1i}$ can be re-calculated into a number of sample using the sampling frequency, i.e. $s_{1i}=f_s\Delta t_{1i}$. The time synchronized sample sets for the N implantable electrodes 211-218 can be represented as a matrix:

$$\begin{pmatrix} s_1^1 & s_2^1 & \cdots & s_{m-1}^1 & s_m^1 \\ s_{1+s_{12}}^2 & s_{2+s_{12}}^2 & \cdots & s_{m-1+s_{12}}^2 & s_{m+s_{12}}^2 \\ \vdots & \vdots & \ddots & \vdots & \vdots \\ s_{1+s_{1N-1}}^{N-1} & s_{2+s_{1N-1}}^{N-1} & \cdots & s_{m-1+s_{1N-1}}^{N-1} & s_{m-1+s_{1N-1}}^{N-1} \\ s_{1+s_{1N}}^N & s_{2+s_{1N}}^N & \cdots & s_{m-1+s_{1N}}^N & s_{m+s_{1N}}^N \end{pmatrix}$$

If the timer would not have been used the lower right portion of the matrix would have been empty since no collected electrogram samples would have been available for the implantable electrodes that are positioned furthest from the implantable electrode, at which the electrical wavefront is first sensed.

The value of this preset timer could be fixed and correspond to a time interval that is determined to be sufficient to capture the necessary electrogram data at all implantable electrodes 211-218. However, in order to optimize the amount of electrogram samples that need to be collected, the timer can advantageously be dynamically set based on the heart rate of the patient. In such a case, the IMD 100 comprises a heart rate estimator 124 for estimating the heart rate based on the electrical activity of the ventricle detected by at least one of the implantable electrodes 211-218. A connected time parameter processor 126 determines the timer or time parameter $T_E$ based on the estimated heart rate. Generally, the higher heart rate, the smaller this timer can be. However, the value of the time parameter is preferably chosen so that it is greater than $\Delta t_{1i}$ for all implantable electrode $i=1\ldots N$ so that there always be sample values at all positions in the shifted matrix presented above.

In an alternative approach, the wavefront detector 122 is arranged for detecting the electrical wavefront at each of the implantable electrodes 211-218. This means that the wavefront detector 122 will, during a given cardiac cycle, generate at least N control signals to trigger the sampling unit 120 to start the recording individually at the different implantable electrodes 211-218. Thus, the starting time for the sampling recording is individually determined for each implantable electrode 211-218 based on when the electrical wavefront arrives that the particular electrode site at the ventricle.

Correspondingly, the sample unit 120 can individually stop the recording at the N implantable electrodes 211-218 based on reception of control signals generated by the wavefront detector 122 upon detection of the following wavefront at the respective implantable electrodes 211-218.

The sample processor 140 of the IMD 100 preferably sums the respective magnitude potential representations of the time synchronized electrogram samples to get a summed sample set. Thus, assume that the time synchronized sample set are represented by the above presented matrix, then the summed sample set can be represented by the following vector ss:

$$ss = \left( |s_1^1| + \sum_{i=2}^{N} |s_{1+s_{1i}}^i| |s_2^1| + \sum_{i=2}^{N} |s_{2+s_{1i}}^i| \ldots |s_{m-1}^1| + \sum_{i=2}^{N} |s_{m-1+s_{1i}}^i| |s_m^1| + \sum_{i=2}^{N} |s_{m+s_{1i}}^i| \right)$$

The parameter indicative of late potentials can then be determined based on the summed sample set.

In a first embodiment only selected sample positions in the matrix are summed. The reason for this is that the QRS complex will by far be the largest signal contribution in each recording with respect to both amplitude and duration. It is further known that late potentials occur after the QRS in the cardiac cycle. This means that the electrogram samples in each sample set corresponding to the QRS complex can simply omitted from the summation. As a consequence, the first columns in the matrix are ignored up until the first column which contains electrogram data after the QRS complex. Furthermore, VLPs often occur at the heart from about 10 ms to about 125 ms after the QRS. This means that only the samples in each time synchronized sample set that corresponds to this time interval need to be analyzed and summed as presented above to remove the non-relevant electrogram data.

This can actually be affected by setting all the electrogram samples in the samples set corresponding to the QRS complex to zero to achieve a blanking of these electrogram samples. The IMD 100 preferably comprises a sample identifier 132 that is implemented for conducting this sample identification and blanking.

Correspondingly, the sample identifier 132 may additionally and/or alternatively be used for identifying and blanking any electrogram samples that occur well after any late potentials. The sample identifier 132 could therefore identify, in each sample set, those electrogram samples that follow an end sample identified to correspond to a predefined electrical characteristic of an electrogram. These identified last electrogram samples are then blanked by setting their values equal to zero. The predefined electrical characteristic could for instance be the T wave, the end or beginning thereof, etc.

FIG. 7 graphically illustrates the process of time aligned electrogram samples from three different sample set after blanking of the electrogram samples corresponding to the QRS and the T wave. In FIG. 8 the magnitude potential representations of the electrogram samples have been summed to get the summed sample set. It is clear from the figure that removal of the QRS samples through the blanking and the summing of the magnitude potential representations magnifies the VLPs and simplifies the detection thereof.

The parameter processor 150 can, according to different embodiments, determine various parameters indicative of late potentials. In a first embodiment, the parameter processor 150 integrates the summed potential representations of the summed sample set to get a single value indicative of late potentials. This integration basically corresponds to the area under the curve in FIG. 8. With the summed sample set as defined according to above, the integration can be defined, following blanking of QRS samples and optionally of electrogram samples corresponding to the T wave and following parts of the cardiac cycle, according to below:

$$\sum_{i=1}^{m} ss_i = |s_1^1| + \sum_{i=2}^{N} |s_{1+s_{1i}}^i| + |s_2^1| + \sum_{i=2}^{N} |s_{2+s_{1i}}^i| + \ldots |s_{m-1}^1| + \sum_{i=2}^{N} |s_{m-1+s_{1i}}^i| + |s_m^1| + \sum_{i=2}^{N} |s_{m+s_{1i}}^i|$$

Another useful parameter could be the length of the curve illustrated in FIG. 8. In both these cases, the higher the value of the parameter the larger the risk for late potentials and the more abundant late potentials.

The IMD 100 can be configured for automatically performing a test for detecting late potentials and thereby a risk of arrhythmias. In such a case, the IMD 100 can perform the above described procedure to generate the parameter indicative of late potentials periodically, such as once a day, twice a day, more often or even more seldom such as once a week. Alternatively, or additionally, the IMD 100 can perform the recording and processing on-demand. In such a case the IMD 100 comprises a receiver, typically in the form of a transmitter/receiver 170 or a transceiver with connected antenna 175. The antenna 175 can be an inductive antenna or a radio frequency antenna as non-limiting examples. In such a case, a non-implantable unit, such as the programmer illustrated in FIG. 1, can generate and transmit a recording command to the IMD 100. The command is received by the receiver 170 and triggers the sampling unit 120 to start recording electrogram samples as previously described.

In an optional embodiment the IMD 100 includes an arrhythmia risk evaluator 152 implemented to detect a potential arrhythmia risk of the heart based on the parameter indicative of late potentials determined by the parameter processor 150. This risk evaluation can be conducted by following trends in any changes in the parameter and a significant risk for arrhythmia is determined if a newly determined parameter significantly differs from previously determined parameters, such as by at least 10-15%. FIG. 9 is a diagram illustrating this concept. The diagram plots determined parameters for different measuring times. As can be seen in the figure, the parameter is fairly constant for the first measurement instances but then abruptly increases. Such a sudden increase is associated with a significant risk for arrhythmias. This means that the IMD 100 can automatically be used for identifying a patient in risk of having arrhythmias, such as ventricular tachycardia or even fibrillation, based on the parameter indicative of late potentials.

The risk evaluator 152 preferably performs the comparison between a newly determined parameter and at least one corresponding parameter determined at a previous measurement time. In a particular embodiment, a parameter threshold is determined based on an average, possibly a weighted average, of previously determined parameters stored in a memory 160 of the IMD 100. The parameter is then compared to the parameter threshold and if there is no significant difference therebetween, such as 10-15% difference, the parameter threshold can optionally be updated by the risk evaluator using the newly acquired parameter. If there is a significant difference and thereby a heightened risk for arrhythmia different actions can be taken.

In a first embodiment, the IMD 100 stores the parameter in the memory 160 possibly together with an indication that it significantly differed from the parameter threshold. In such a case, the physician can later on upload the data from the IMD 100 using the transmitter 170 and antenna 175.

Alternatively, the determined parameter and possibly the indication are transmitted to a non-implantable unit capable of conducting wireless communication with the IMD 100. This non-implantable unit could be a home monitoring unit or a portable communication unit worn by the patient. In such a case, the unit can indicate to the patient that he/she should immediately visit or contact his/her physician and inform him/her of the detected arrhythmia risk. The non-implantable unit could alternatively or additionally automatically forward the received data from the IMD 100 to the physician using a wired or wireless communication network.

The IMD 100 could be equipped with an alarm unit (not shown) that raises an alarm that can be detected by the patient in which the IMD 100 is implanted. The alarm is typically a tactile and/or audio alarm.

A further embodiment provides an IMD 100 with an anti-arrhythmia unit 154. This anti-arrhythmia unit 154 is connected to both the risk evaluator 152 and the electrode I/O 110 and triggers an anti-arrhythmia treatment scheme if the risk evaluator 152 generates and transmits a trigger signal indicative of a sudden risk of arrhythmia. The anti-arrhythmia treatment is typically affected through the delivery of electrical signals to at least a portion of the heart using implantable electrodes 211-218 connected to the IMD 100. Such anti-arrhythmia electric signals are well known in the art and not further described herein.

The IMD 100 can also be equipped according to any combination of at least two of the above presented alternatives.

The memory 160 of the IMD 100 is used to store all the data necessary during the process of determining the parameter indicative of late potentials. This means that all the raw data used by the IMD 100 can be stored in the memory 160 and possibly later uploaded to the programmer. However, the present invention actually minimizes the amount of data that needs to be stored by merely storing the parameter determined by the parameter processor. This means that all the raw data collected by the sampling unit and further processed by the sample synchronizer 130, the sample processor 140 and the parameter processor 150 can be removed from the memory 160 once the parameter has been correctly determined.

The IMD 100 also comprises a battery 180 providing the power required for running the other units of the IMD 100, which is well known in the art.

The units 110-154, 170 of the IMD 100 may be implemented in hardware, software or a combination of hardware and software. In FIG. 2 and the discussion of embodiments above, reference has only been to the IMD units directly involved in the present invention. It is therefore anticipated by the invention that the IMD 100 typically comprises other units and functionalities required for efficient and correct operation of the IMD 100.

Figure 3:
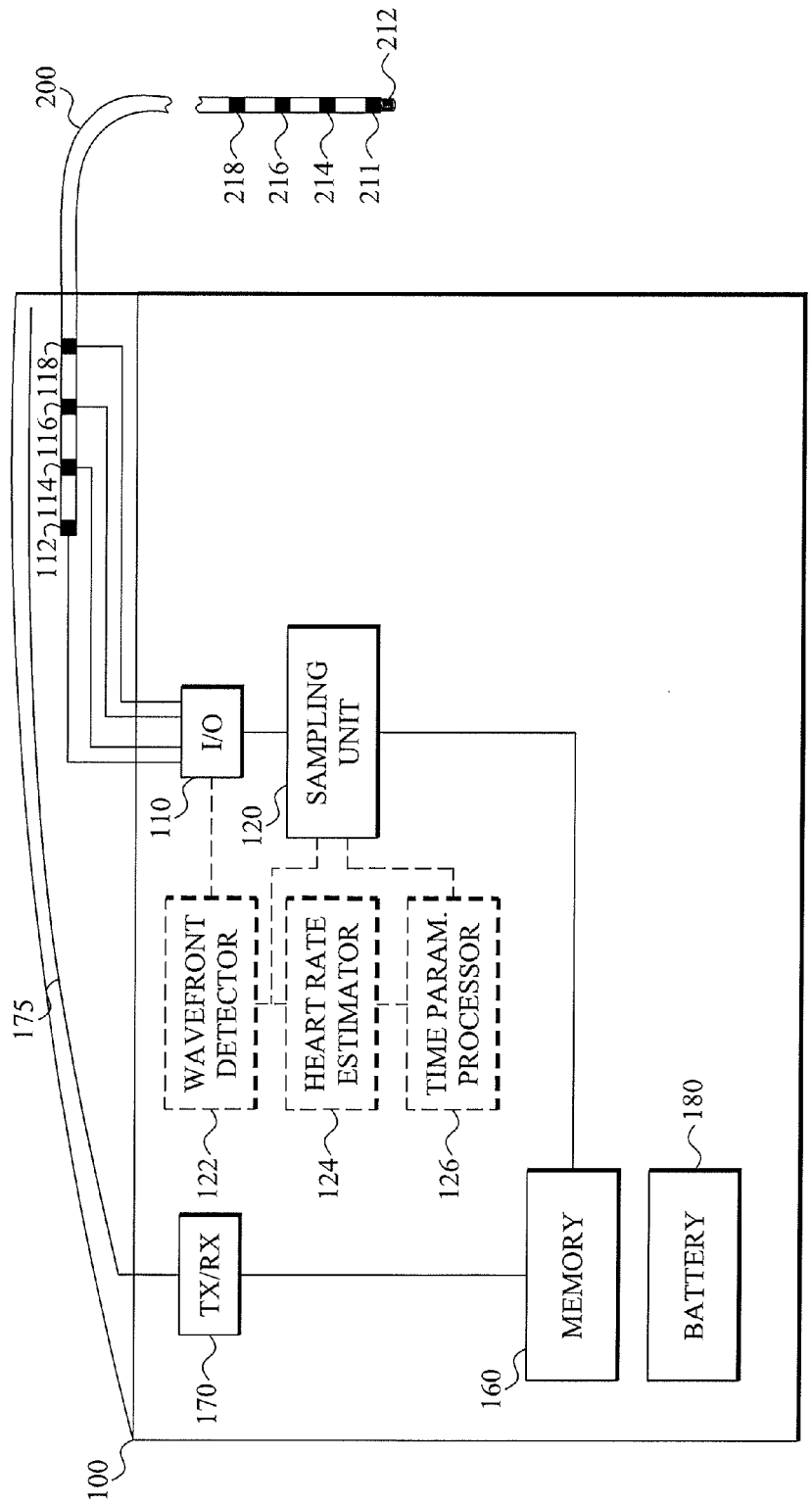
FIG. 3 is a schematic block diagram of an implantable medical device constituting a unit of a late potential detecting system.
Figure 4:
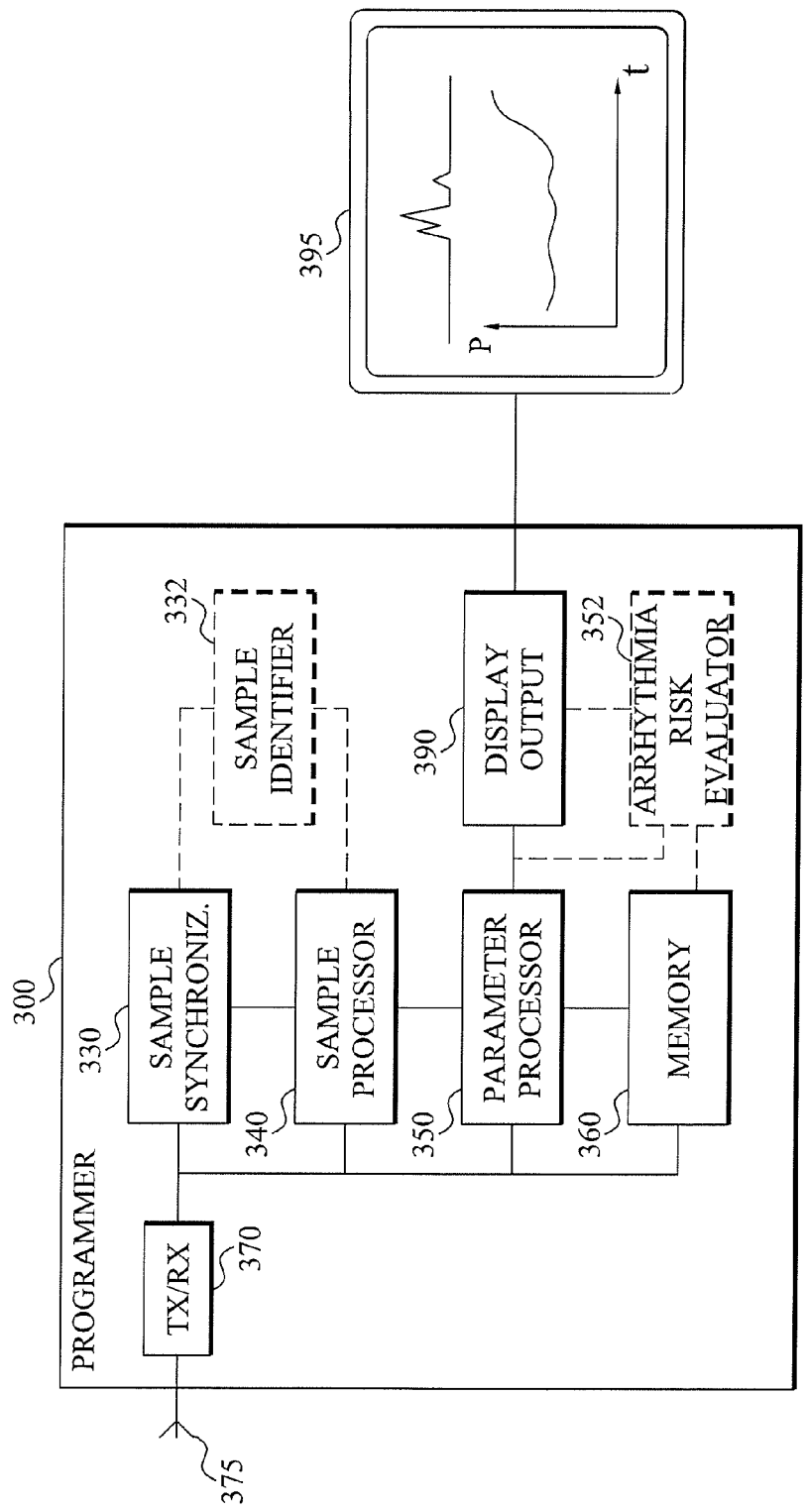
FIG. 4 is a schematic block diagram of a non-implantable data processing terminal constituting another unit of the late potential detecting system together with the implantable medical device of FIG. 3.

FIG. 3 is a schematic block diagram of another embodiment of a part of a late potential detecting system. The system comprises an IMD 100 as illustrated in FIG. 3 and a non-implantable unit, such as programmer as illustrated in FIG. 4. In this embodiment, the IMD 100 is basically used for collecting the raw data, i.e. the electrogram samples of the N sample sets. The processing of the electrogram samples, i.e. the time synchronization, determination of magnitude potential representation and calculation of the parameter indicative of late potentials, is in this embodiment conducted by the non-implantable unit of the late potential detecting system. IMDs 100 generally have limited processing capacity and above all are powered by battery 180. This means that it can sometimes be an advantage to conduct the data processing in the non-implantable unit to thereby save processing capacity and battery power for the IMD 100.

The IMD 100 consequently comprises the previously described electrode I/O 110 and the sampling unit 120. The IMD 100 may optionally also comprise the wavefront detector 122 and optionally the heart rate estimator 124 and the time parameter processor 126. The operations of these units are the same as previously described.

The electrogram samples of the N sample sets recorded by the sampling unit 120 are typically entered in the memory 160 of the IMD 100. The electrogram samples can then be uploaded and transmitted by the transmitter 170 and its antenna 175 to the non-implantable unit. The transmission of the electrogram samples can be conducted according to different embodiments. In a first example, the transmitter 170 sends the data as soon as all the data from a measurement batch has been collected and optionally entered in the memory 160. In another example, the transmitter 170 is scheduled to upload recorded electrogram sample data at predefined time instances. This can for instance be performed during night-time, when the patient is sleeping and the data is automatically uploaded to a home monitoring unit present in the home of the patient. A further example is to only upload the recorded electrogram sample data upon an explicit request from the non-implantable unit. In such a case, the receiver 170 and the antenna 175 receives such a request from the non-implantable unit and triggers the transmitter 170 to start sending the requested data to the non-implantable unit.

FIG. 4 is a schematic block diagram of an embodiment of a non-implantable unit 300 forming a part of the late potential detecting system. In this embodiment, the non-implantable unit 300 has been exemplified by a dedicated programmer 300 capable of interrogating and communicating with the IMD. This should, however, merely be seen as an illustrative example. Other non-implantable units and terminals that can be used according to the invention include home monitoring units, computers, laptops, portable processing units, such as personal digitial assistants (PDAs) and mobile telephones, as long as these have equipment and functionality for communicating with an IMD and in particular receiving electrogram sample data therefrom.

The programmer 300 comprises a transmitter/receiver 370 and connected antenna 375 for communicating with the IMD. The programmer 300 preferably also comprises a memory 360 for storing data received from the IMD and/or the electrogram sample data during the processing thereof by a sample synchronizer 330, sample processor 340 and a parameter processor 350. The operations of the sample synchronizer 330, the sample processor 340, the parameter processor 350 and the optional sample identifier 332 and arrhythmia risk evaluator 352 are basically the same as if the units would have been implemented in the IMD. The discussion above in connection with FIG. 2 consequently applies also to these units even though they are here provided in the programmer 300 instead of the IMD.

The programmer 300 preferably also comprises a display output 390 with included or connected display screen 395. In such a case, visual representations of data relating to the late potential detection can be presented on the display screen 395. For instance, the summed sample set can be displayed to visually indicate the presence of any late potentials in the summed electrogram data. Also the trend in the parameter indicative of late potentials can be visually illustrated as shown in the figure. The display output 390 can further indicate any significant risks of arrhythmia as determined by the arrhythmia risk evaluator 352. The presented information may then simply be a notification or an alarm of increased risk of arrhythmia as assessed based on the detected presence of late potentials, in particular ventricular late potentials, or based on the detected increase in the number/magnitude of late potentials. Alternatively, more detailed risk information can be given, such as the value of the parameter determined by the parameter processor 350, the increase or decrease in the parameter as compared to a parameter threshold, etc.

In alternative embodiments, not all of the sample synchronizer 330, sample processor 340 and parameter processor 350 are provided in the programmer 300. For instance, the sample synchronizer can be implemented in the IMD together with the sampling unit, whereas the sample processor 340 and the parameter processor 350 are implemented in the programmer 300. A further example has the sampling unit, the sample synchronizer and the sample processor in the IMD and the parameter processor 350 is arranged in the programmer 300.

The units 330-352, 370, 390 of the programmer 300 may be implemented in hardware, software or a combination of hardware and software.

A further embodiment of the late potential detecting system comprises three major including units, the IMD, a non-implantable communication unit and a non-implantable processing unit. The IMD could then be designed as illustrated in FIG. 3 and basically collects the raw electrogram sample data. This data is wirelessly transmitted to the non-implantable communicating unit, which can be exemplified by a home monitoring unit, a portable communicating unit, such as PDA or mobile unit. The non-implantable communicating unit generally does not process the received electrogram sample data for the purpose of detecting any late potentials but merely functions as data forwarding unit. The communicating unit is therefore capable of not only wirelessly communicating with the IMD but also communicate with the non-implantable processing unit, such as through a wired or wireless communication network. The processing unit can therefore be a remote data processing unit, such as computer, present at a healthcare facility of the patient's physician. The recorded electrogram sample data is therefore communicated to the physician from the IMD, through the non-implantable communicating unit and to the physician's processing unit.

Figures 10, 11:
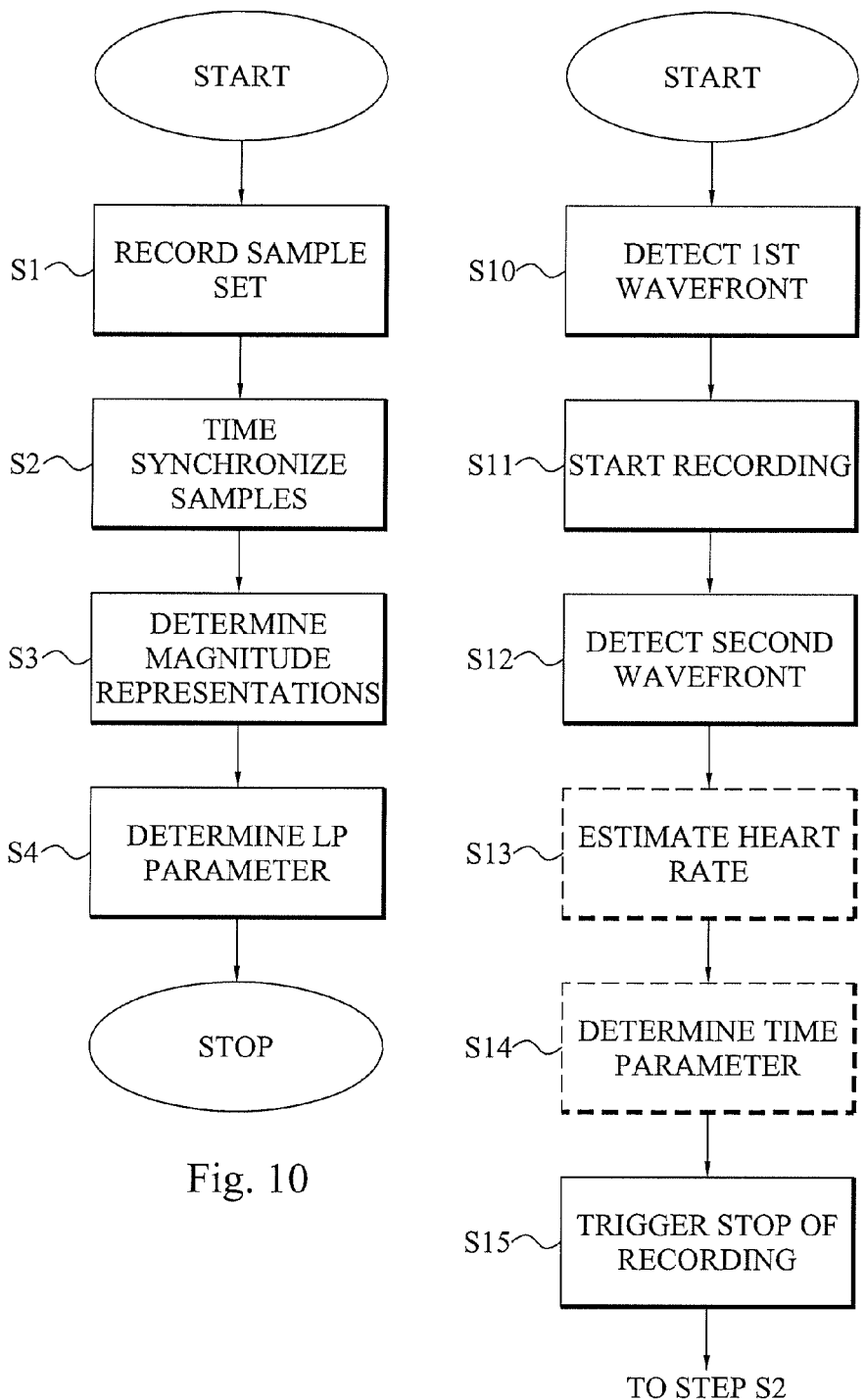
FIG. 10 is a flow diagram illustrating an embodiment of a late potential detecting method.
FIG. 11 is a flow diagram illustrating an embodiment of the recording step in FIG. 10.

FIG. 10 is a flow diagram illustrating a method of detecting late potentials according to an embodiment. The method starts in step S1, which records N sample sets of electrogram samples representing detected electrical activity of the myocardium at different parts of a ventricle during a cardiac cycle. The electrogram samples are time synchronized in step S2 so that electrogram samples corresponding to the same electrical characteristics of an electrogram become time aligned. The time synchronized electrogram samples are processed in step S3 by determining magnitude potential representations of the electrogram samples. The determination of magnitude potential representations of step S3 may be conducted after the time synchronization of the electrogram samples in step S2 as illustrated in the figure. Alternatively, step S3 is performed prior to the time synchronization in step S2. Magnitude potential representations of the time synchronized electrogram samples are co-processed in step S4 and used for determining a parameter indicative of any late potentials occurring in the ventricle during the monitored cardiac cycle.

The steps S1 to S4 can be conducted once, such as based on a request for determination of the parameter. Alternatively, the steps S1 to S4 can be conducted multiple times, such as periodically or at scheduled monitoring time instances, such as once a day, once a week or more often or more seldom. The actual frequency of measurements can be programmed and set by the physician based on the estimated risk the patient has of getting arrhythmias.

FIG. 11 is a flow diagram illustrating an embodiment of the recording step S1 in FIG. 10. The method starts in step S10, where an electrical wavefront, such as depolarization wavefront, is detected at one of the sensing sites of the ventricle myocardium. The detection of the wavefront triggers the start of the recording at all sensing sites in step S11. Once a second wavefront corresponding to the following cardiac cycle is detected at any of the sensing sites in step S12, a stop of the recording is triggered in step S15. Optionally the method may also involve estimating the current heart rate of the heart in step S13 based on sensing the electrical activity of the heart. A time parameter $T_E$ is determined based on the heart rate in step S14. The time parameter is preferably inversely proportional to the estimated heart rate. These steps S13 and S14 can be conducted prior to step S10 or actually any time prior step S15. The triggering step S15 then preferably stops the recording of the electrogram samples at the sensing sites at a time instance $T_E$ time units after the detection of the second wavefront at step S12. The method then continues to step S2 of FIG. 10.

Figure 12:
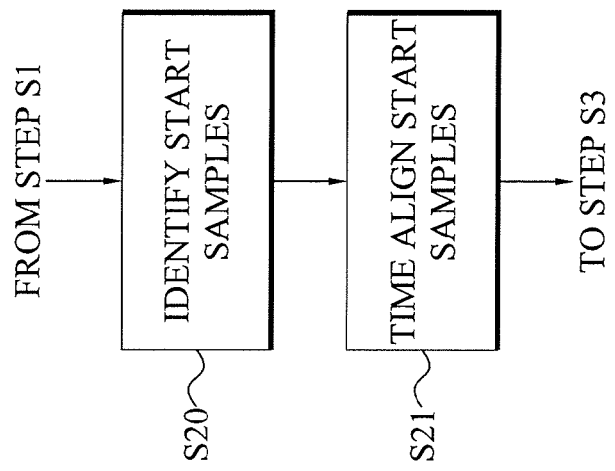
FIG. 12 is a flow diagram illustrating an embodiment of the time synchronizing step in FIG. 10.

FIG. 12 is a flow diagram illustrating an embodiment of the time synchronizing step S2 in FIG. 10. The method continues from step S1 in FIG. 10. A next step S20 identifies a respective start sample in the N sample sets. These start electrogram samples comprise a predefined electrical characteristic of an electrogram, such as a defined portion of a QRS complex, the P wave, the Q wave, the R wave, the S wave or a defined portion of any of these electrical characteristics. The identified start samples are then time aligned in step S21 to achieve the time synchronization of the electrogram samples of the N samples sets. The time alignment can be conducted by marking the identified electrogram samples as start samples. Alternatively, all recorded electrogram samples in the sample sets prior to the identified start samples can be removed so that the start samples will be the first electrogram samples in each sample set. The method then continues to step S3 of FIG. 10.

FIG. 13 is a flow diagram illustrating additional optional steps of the late potential identifying method. The method continues from step S30, which identifies those electrogram samples in the sample sets that corresponds to the electrical activity of the QRS complex. These samples can be easily identified as they by far have the highest potential magnitude of the recorded electrogram samples during a cardiac cycle. The identified QRS electrogram samples are omitted from the sample sets or are blanked in step S31 by setting the sample values equal to zero for those electrogram samples that were identified in step S30. Thereby the contribution of the QRS complex to the electrogram data is removed. A similar removal or blanking of electrogram samples can optionally be conducted for those electrogram samples of the sample sets that correspond to the T wave and any following electrogram samples. This is possible since any late potentials are most often present in the time window of the cardiac cycle occurring after the QRS complex but before the T wave.

The next step S32 sums the magnitude potential representations of at least a portion of the electrogram samples from the N sample sets. In a first embodiment, those electrogram samples that most likely contain any late potentials, i.e. those occurring after the QRS complex but before the T wave, are only processed in step S32. In an alternative embodiment that is particularly suitable for usage in connection with sample blanking in step S31 all remaining electrogram samples in the N sample sets are used in step S32. Step S32 involves summing one electrogram sample from each of the sample sets. Since the sample sets have been time synchronized in step S2 of FIG. 10, the electrogram samples have been time aligned to represent substantially the same time windows of the cardiac cycle. This means that step S32 sums the magnitude potential representations of the first electrogram samples in the sample sets to get a first summed electrogram sample, sums the magnitude potential representations of the second electrogram samples in the sample sets to get a second summed electrogram sample, and so on. The result of this sample summation in step S32 is a summed sample set that is used for determining the parameter indicative of late potentials.

Step S33 illustrates an embodiment of determining the parameter. In this embodiment the summed magnitude potential representations are integrated to get the parameter. This integration can be conducted by summing the respective magnitude potential representations of the electrogram samples to get a single value:

$$\hat{P} = \sum_{i=1}^{m} ss_i, \text{ where } ss = [\, ss_1 \quad ss_2 \quad \ldots \quad ss_{m-1} \quad ss_m \,]$$

represents the summed sample set. Alternatively, the length of the curve defined by the summed sample set can be determined and used as parameter, such as $$\hat{P} = \sum_{i=1}^{m-1} |ss_{i+1} - ss_i|.$$

The method then continues to step S4 of FIG. 10.

FIG. 14 is a flow diagram illustrating additional optional steps of the late potential detecting method. Step S40 monitors, based on the parameter indicative of late potentials, whether there is a potential risk of an arrhythmia condition, in particular ventricular tachycardia or fibrillation. This monitoring is preferably performed by comparing the determined parameter with a parameter threshold and an arrhythmia risk is detected if the parameter differs significantly from the parameter threshold, such as by at least 10-15%. If the parameter is determined as described in the foregoing, e.g. by integrating or summing the magnitude potential representations of the summed sample set, there is a potential arrhythmia risk if the parameter exceeds the parameter threshold with the predefined minimum amount, such as 10-15%.

If no arrhythmia risk is detected in step S40, the parameter threshold is optionally updated based on the newly determined parameter. This is in particular advantageous if the parameter threshold is determined as an average of previously determined parameters indicative of late potentials, possibly a weighted average with larger weights for more recently determined parameters. In such a case, the parameter threshold is preferably recalculated using also the most recent parameter. This parameter updating can be advantageous as there may be slowly changing conditions in the heart that are not relating to late potentials or arrhythmia risks but that affects the recording of the electrogram samples. For instance, following implantation inflammatory reactions often occur around the electrodes in the myocardium, which can affect the sensing of electrical activity of the myocardium. Additionally, connective tissue can grow around implanted electrodes, which also affects the sensing.

If it is determined that there is a significant risk of an arrhythmia condition due to the presence of late potentials, an alarm can be run in step S41. The alarm can be made by the IMD itself, such as in the form of a tactile and/or audio alarm. Alternatively, the IMD generates and transmits an alarm signal to a non-implantable unit capable of communicating with the IMD to thereby inform the patient and/or a physician of the eminent risk of arrhythmia. If the parameter determination and arrhythmia risk assessment is conducted by a non-implantable unit, the alarm is preferably run or notified on that unit.

An optional further step S42 initiates anti-arrhythmia actions by the IMD, such as in the form of applying an anti-arrhythmia treatment pacing sequence to the heart. Such treatment trigger can be conducted automatically based on the risk detection in step S40, i.e. without the need of informing the physician. Alternatively, the treatment sequence is only triggered upon reception of a triggering command by the IMD from a non-implantable unit, which is preferably controlled by the physician. The physician has then concluded that such anti-arrhythmia treatment is needed based on the high risk of arrhythmia as concluded based on the parameter indicative of late potentials.

The method then ends.

Although modifications and changes may be suggested by those skilled in the art, it is the intention of the inventor to embody within the patent warranted heron all changes and modifications as reasonably and properly come within the scope of his contribution to the art.

I claim as my invention:

1. A late potential detecting system comprising:
    an implantable medical device having an electrode input comprising at least N electrode terminals electrically connectable to at least N implantable electrodes arrangeable for detecting electrical activity of the myocardium at different parts of a ventricle of a heart, where N≥2, and a sampling unit connected to said electrode input and configured for recording, for each of N implantable electrodes, a sample set of electrogram samples representing detected electrical activity of said myocardium during a cardiac cycle;
    a sample synchronizer configured to time-synchronize said electrogram samples of said N sample sets;
    a sample processor configured to determine, for each of said N sample sets, magnitude potential representations of electrogram samples;
    a parameter processor configured to determine, based on said magnitude potential representations from said N sample sets, a parameter indicative of late potentials occurring during said cardiac cycle for said ventricle;
    a wavefront detector connected to said electrode input and configured for detecting an electrical wavefront at an implantable electrode of said N implantable electrodes and for generating a control signal upon detection of said electrical wavefront, wherein said sampling unit is responsive to said control signal and is configured for starting recording said N sample sets based on reception of a first control signal from said wavefront detector and triggering a stop of the recording of said N sample sets based on reception of a second, subsequent control signal from said wavefront detector;
    a heart rate estimator configured to estimate a heart rate of said heart based on electrical activity of said ventricle detected by at least one implantable electrode of said at least N implantable electrodes; and
    a time parameter processor configured to determine a time parameter $T_E$ representative of said heart rate estimated by said heart rate estimator, wherein said sampling unit is configured for stopping recording of said N sample sets at a time instance $T_E$ time units after reception of said second, subsequent control signal from said wavefront detector.

2. A late potential detecting system comprising:
an implantable medical device having an electrode input comprising at least N electrode terminals electrically connectable to at least N implantable electrodes arrangeable for detecting electrical activity of the myocardium at different parts of a ventricle of a heart, where N≥2, and a sampling unit connected to said electrode input and configured for recording, for each of N implantable electrodes, a sample set of electrogram samples representing detected electrical activity of said myocardium during a cardiac cycle;
a sample synchronizer configured to time-synchronize said electrogram samples of said N sample sets;
a sample processor configured to determine, for each of said N sample sets, magnitude potential representations of electroqram samples;
a parameter processor configured to determine, based on said magnitude potential representations from said N sample sets, a parameter indicative of late potentials occurring during said cardiac cycle for said ventricle;
a wavefront detector connected to said electrode input and configured to detect an electrical wavefront at said N implantable electrodes and for generating a control signal upon detection of said electrical wavefront, wherein said sampling unit is responsive to said control signal and is configured for starting recording, for an implantable electrode of said N implantable electrodes, said sample set based on reception of a control signal from said wavefront detector generated upon detection of said electrical wavefront at said implantable electrode;
a heart rate estimator configured to estimate a heart rate of said heart based on electrical activity of said ventricle detected by at least one implantable electrode of said at least N implantable electrodes; and
a time parameter processor configured to determine a time parameter $T_E$ representative of said heart rate estimated by said heart rate estimator, wherein said sampling unit is configured for stopping recording of said N sample sets at a time instance $T_E$ time units after reception of said second, subsequent control signal from said wavefront detector.

3. The late potential detecting system according to claim 2, wherein said sample synchronizer is configured for identifying, for each of said N sample sets, a start electrogram sample comprising a predefined electrical characteristic of an electrogram and for synchronizing said electrogram samples of said N sample sets so that said N start electrogram samples are time aligned.

4. The late potential detecting system according to claim 3, wherein said sample synchronizer is configured to identify, for each of said N sample sets, a start electrogram sample corresponding to the start of a QRS complex.

5. The late potential detecting system according to claim 2, wherein said sample processor is configured to determine, for each of said N sample sets, absolute potential values of said electrogram samples.

6. The late potential detecting system according to claim 2, further comprising a sample identifier configured for identifying, for each of said N sample sets, electrogram samples corresponding to a QRS complex and for blanking said electrogram samples identified as corresponding to said QRS complex.

7. The late potential detecting system according to claim 2, further comprising a sample identifier configured for identifying, for each of said N sample sets, electrogram samples present in said each sample set following an end sample corresponding to a predefined electrical characteristic of an electrogram and for blanking said electrogram samples identified by said sample identifier.

8. A late potential detecting system comprising:
an implantable medical device having an electrode input comprising at least N electrode terminals electrically connectable to at least N implantable electrodes arrangeable for detecting electrical activity of the myocardium at different parts of a ventricle of a heart, where N≥2, and a sampling unit connected to said electrode input and configured for recording, for each of N implantable electrodes, a sample set of electrogram samples representing detected electrical activity of said myocardium during a cardiac cycle;
a sample synchronizer configured to time-synchronize said electrogram samples of said N sample sets;
a sample processor configured to determine, for each of said N sample sets, magnitude potential representations of electrogram samples; and
a parameter processor configured to determine, based on said magnitude potential representations from said N sample sets, a parameter indicative of late potentials occurring during said cardiac cycle for said ventricle;
wherein said parameter processor is configured for summing magnitude potential representations of corresponding electrogram samples for said N sample sets to get a summed sample set comprising electrogram samples of summed magnitude potential representations and for determining, based on said summed sample set, said parameter indicative of said late potentials.

9. The late potential detecting system according to claim 8, wherein said parameter processor is configured to determine said parameter indicative of said late potentials by integrating said summed potential representations of said summed sample set.

10. The late potential detecting system according to claim 8, wherein said electrode input is electrically connectable to a proximal end of a multi-electrode cardiac lead carrying said N implantable electrodes at a distal lead portion and N≥4.

11. The late potential detecting system according to claim 8, further comprising a memory for storing said parameter indicative of said late potentials.

12. The late potential detecting system according to claim 8, further comprising an arrhythmia risk evaluator configured for detecting a potential arrhythmia risk of said heart based on a comparison of said parameter indicative of said late potentials and a parameter threshold.

13. The late potential detecting system according to claim 12, wherein said parameter processor is configured to determine said parameter threshold based on a previously determined parameter representative of late potentials occurring during a previous cardiac cycle for said ventricle.

14. The late potential detecting system according to claim 8, wherein said sample synchronizer, said sample processor and said parameter processor are arranged in said implantable medical device.

15. The late potential detecting system according to claim 8, wherein said implantable medical device further comprises a transmitter connected to an antenna and arranged for transmitting information of said electrogram samples of said N sample sets to a non-implantable data processing terminal of said late potential detecting system, said sample synchronizer, said sample processor and said parameter processor are arranged in said non-implantable data processing terminal.

16. A method of detecting late potential comprising:
recording N sample sets of electrogram samples representing detected electrical activity of myocardium at different parts of a ventricle of a heart during a cardiac cycle, where N≥2;
time synchronizing said electrogram samples of said N sample sets;
determining, for each of said N sample sets, magnitude potential representations of electrogram samples;
determining, based on said magnitude potential representations from said N sample sets, a parameter indicative of late potentials occurring during said cardiac cycle for said ventricle;
estimating a heart rate of said heart based on detected electrical activity of said ventricle; and
determining a time parameter $T_E$ representative of said heart rate, wherein said triggering step comprises stopping recording of said N sample sets at a time instance $T_E$ time units after detection of said second, subsequent electrical wavefront;
wherein said recording comprises:
detecting a first electrical wavefront at an implantable electrode of N implantable electrodes;
starting recording said N sample sets based on the detection of said first electrical wavefront;
detecting a second, subsequent electrical wavefront at said implantable electrode; and
triggering a stop of recording said N sample sets based on the detection of said second, subsequent electrical wavefront.

17. The method according to claim 16, wherein said time synchronizing comprises:
identifying, for each of said N sample sets, a start electrogram sample comprising a predefined electrical characteristic of an electrogram; and
synchronizing said electrogram samples of said N sample sets so that said N start electrogram samples are time aligned.

18. The method according to claim 16, further comprising:
identifying, for each of said N sample sets, electrogram samples corresponding to a QRS complex; and
blanking said electrogram samples identified as corresponding to said QRS complex.

19. The method according to claim 16, further comprising:
identifying, for each of said N sample sets, an end electrogram sample corresponding to a predefined electrical characteristic of an electrogram; and
blanking electrogram samples following said identified en electrogram sample.

20. A method of detecting late potential comprising:
recording N sample sets of electrogram samples representing detected electrical activity of myocardium at different parts of a ventricle of a heart during a cardiac cycle, where N≥2;
time synchronizing said electrogram samples of said N sample sets;
determining, for each of said N sample sets, magnitude potential representations of electrogram samples; and
determining, based on said magnitude potential representations from said N sample sets, a parameter indicative of late potentials occurring during said cardiac cycle for said ventricle;
wherein said determining parameter comprises:
summing magnitude potential representations of corresponding electrogram samples for said N sample sets to get a summed sample set comprising electrogram samples of summed magnitude potential representations; and
determining, based on said summed sample set, said parameter indicative of said late potentials.

21. The method according to claim 20, wherein said determining said parameter comprises determining said parameter indicative of said late potentials by integrating said summed potential representations of said summed sample set.

22. The method according to claim 20, further comprising detecting a potential arrhythmia risk of said heart based on a comparison of said parameter indicative of said late potentials and a parameter threshold.

\* \* \* \* \*